United States Patent [19]

Sanderson et al.

[11] Patent Number: 4,992,602
[45] Date of Patent: Feb. 12, 1991

[54] PREPARATION OF TERTIARY BUTYL ALCOHOL

[75] Inventors: John R. Sanderson, Leander; Edward T. Marquis, Austin, both of Tex.

[73] Assignee: Texaco Chemical Company, White Plains, N.Y.

[21] Appl. No.: 471,751

[22] Filed: Jan. 29, 1990

[51] Int. Cl.⁵ .................. C07C 29/132; C07C 29/50; C07C 31/12; C07C 29/00
[52] U.S. Cl. .................................. 568/909.8; 568/910
[58] Field of Search ........................ 568/909.8

[56] References Cited

U.S. PATENT DOCUMENTS 3,505,360  4/1970  Allison et al. ............... 568/909.8
3,928,452  12/1975 Brunie et al. ............... 568/909.8
4,910,349  3/1990  Sanderson et al. ........... 568/909.8
4,912,266  3/1990  Sanderson et al. ........... 568/909.8
4,912,267  3/1990  Sanderson et al. ........... 568/909.8
4,922,033  5/1990  Sanderson et al. ........... 568/909.8
4,922,034  5/1990  Sanderson et al. ........... 568/909.8
4,922,035  5/1990  Sanderson et al. ........... 568/909.8
4,922,036  5/1990  Sanderson et al. ........... 568/909.8

*Primary Examiner*—J. E. Evans
*Attorney, Agent, or Firm*—Jack H. Park; Kenneth R. Priem; Carl G. Ries

[57] ABSTRACT

Tertiary butyl alcohol is prepared by the catalytic decomposition of tertiary butyl hydroperoxide in solution in a monocyclic aromatic solvent in the presence of a metal phthalocycnaine catalyst.

9 Claims, No Drawings

PREPARATION OF TERTIARY BUTYL ALCOHOL

BACKGROUND OF THE INVENTION

1. Field of the Invention

This invention relates to the catalytic decomposition of tertiary butyl hydroperoxide. More particularly, this invention relates to a method for the preparation of tertiary butyl alcohol by the catalytic decomposition of tertiary butyl hydroperoxide.

Still more particularly, this invention relates to an improved continuous method for the preparation of tertiary butyl alcohol wherein a solution of tertiary butyl hydroperoxide in tertiary butyl alcohol formed by the reaction of isobutane with oxygen is separated into a tertiary butyl alcohol fraction and a concentrated tertiary butyl hydroperoxide fraction, wherein the concentrated tertiary butyl hydroperoxide fraction is dissolved in a monocyclic aromatic solvent to form a solution, and wherein the solution is charged to a tertiary butyl hydroperoxide decomposition zone together with a phthalocyanine catalyst and substantially selectively decomposed therein to tertiary butyl alcohol.

2. Prior Art

It is known to react isobutane with oxygen, either thermally or catalytically, to form a peroxidation reaction product wherein the principal peroxide that is formed is tertiary butyl hydroperoxide. It is also known to thermally or catalytically decompose the tertiary butyl hydroproxide to form tertiary butyl alcohol.

Taylor et al. U.S. Pat. No. 4,551,553 is directed to a process for the formation of alcohols such as tertiary butyl alcohol by the catalytic decomposition of an organic hydroperoxide such as tertiary butyl hydroperoxide using a binary catalyst composed of a mixture of a ruthenium compound with a chromium compound. It is stated that the use of the binary catalyst eliminates the need for stabilizing ligands.

Klein in U.S. Pat. No. 3,472,876, discloses the use of cobalt diimine chelates to catalyze the reaction of oxygen with an olefin to form an olefin epoxide.

Quin U.S. Pat. No. 2,854,487 discloses a process wherein isopropyl benzene hydroperoxides are catalytically decomposed to form carbonols in the presence of hydrogen and a catalyst composed of palladium supported on activated alumina.

Grane U.S. Pat. No. 3,474,151 discloses that tertiary butyl alcohol starts to dehydrate at 450° C. and to decompose at a "rapid rate" at temperatures above 475° F. Grane discovered, however, that residual quantities of hydroperoxide contaminants present in tertiary butyl alcohol could be thermally decomposed by heating the contaminated tertiary butyl alcohol at a temperature of 375° to 475° F. for about 1 to 10 minutes.

Grane et al. U.S. Pat. No. 4,294,999 discloses a process wherein isobutane is oxidized in a pressured reactor in the presence of a solubilized molybdenum catalyst to provide a mixture of tertiary butyl alcohol, tertiary butyl hydroperoxide, methanol, acetone, and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane U.S. Pat. No. 3,474,151 by heating the tertiary butyl alcohol at 375° to 475° for about 1 to 10 minutes. Heating tertiary butyl alcohol containing small amounts of peroxides at high temperatures for even short periods of time to remove the peroxides produces undesirable products such as isobutylene.

Grane et al. U.S. Pat. No. 4,296,262 discloses a related process wherein isobutane is reacted with oxygen in a reaction zone for a residence time of about 1 to 10 hours at a temperature of about 240° to about 340° F. and a pressure of about 100 to about 1000 psig. in the presence of a catalytically effective amount of a soluble molybdenum catalyst. A liquid stream comprising tertiary butyl alcohol is recovered from the reaction mixture and fed to a decomposition zone wherein the tertiary butyl hydroperoxide contained therein is decomposed by "hot aging" at 250°-350° F. at a pressure lower than the pressure in the oxidation zone. The tertiary butyl alcohol can be further subjected to a cleanup treatment at 375°-475° F. for 1 to 10 minutes. Worrell et al. in U.S. Pat. No. 4,296,263 discloses a related process wherein the feedstock is a mixture of normal butane with isobutane and wherein the oxidation catalyst is a soluble form of chromium, cobalt, nickel, manganese, molybdenum, or a mixture thereof.

The metal phthalocyanines are known compounds, described for example in the ACS Monograph Series of F. H. Moser and A. L. Thomas entitled "Phthalocyanine Compounds" (Rhinehold Publishing Corp.).

Williams et al. U.S. Pat. No. 3,816,548 is directed to a liquid phase oxidation process for oxidizing an isoparaffin hydrocarbon such as isobutane to an alcohol such as tertiary butyl alcohol in the presence of certain metal phthalocyanine catalysts.

Allison et al. U.S. Pat. No. 3,505,360 states that it has been reported that cyclohexenyl hydroperoxide has been decomposed to provide cyclohexanone and cyclohexanol in the presence of ferrous phthalocyanine.

Ohkatsu et al., in an article entitled "The Liquid-Phase Oxidation of Acetaldehyde with Metal Phthalocyanines. Solvent Effect", *Bulletin of the Chemical Society of Japan*, Vol. 50 (3) 696-700 (1977), report on their investigation of the effect of the solvent used when oxidizing acetaldehyde with oxygen using a metal phthalocyanine catalyst and their conclusion that the solvent effects the rate of oxidation in two ways, one based on the prevention of the oxygen molecules from coordinating with the metal phthalocyanine and the other due to the solvation with the activated oxygen molecules on the catalyst molecule. Preferred solvents were ethyl acetate, bromobenzene, benzene and acetone.

Sheng et al., in an article entitled "Hydroperoxide Oxidations Catalyzed by Metals", *Advances in Chemistry Series*, 76, 418 (1968), conclude that in the reaction of an organic hydroperoxide with an olefin in the presence of a vanadium, molybdenum or tungsten catalyst, the conversion and epoxide yield are higher, in general, as the polarity of the solvent decreases. Benzene was one of the solvents that was used.

An article entitled "Metal-Catalyzed Epoxidation of Olefins with Organic Hydroperoxides" by Sheldon et al., *Journal of Catalysts*, 31, 427-437 (1979) on pages 30 and 31, reports on the results obtained by the Metal-Catalyzed Decomposition of Tertiary Butyl Hydroperoxide in the absence of an olefin including the decomposition of tertiary butyl hydroperoxide in solution in benzene in the presence of Mo, Ti, W and Cr catalysts to provide tertiary butyl alcohol and oxygen.

BACKGROUND INFORMATION

When isobutane is reacted with molecular oxygen, the principal products of the reaction are tertiary butyl alcohol and tertiary butyl hydroperoxide. Minor quantities of other contaminants including ditertiary butyl peroxide are also formed.

In addition, a minor amount of water will be formed, which will normally amount to about 0.5 to 1 wt.% of the reactor effluent. The amount of by-product water that is produced is a function of the severity of the reaction conditions employed and will tend to increase as the severity of the reaction conditions is increased.

A listing of the components present in a representative reaction product, and their nominal boiling points is given in Table A.

TABLE A

| Component | NBP (°C.) |
|---|---|
| Isobutane | −11.7 |
| Methyl formate | 31.8 |
| Acetone | 56.3 |
| Isobutylene Oxide | 60.0 |
| Isobutyraldehyde | 64.1 |
| Methanol | 64.7 |
| Methyl-t-butyl peroxide | 74.2 |
| Isopropyl alcohol | 82.3 |
| Tertiary butyl alcohol | 82.4 |
| Ditertiary butyl peroxide | 111.0 |
| t-butyl-i-pr-peroxide | 124.0 |
| Tertiary butyl formate | 163.8 |

The minor by-products are difficult to remove. For example, tertiary butyl formate has a higher boiling point that ditertiary butyl hydroperoxide but tends to distill overhead, which suggests that it forms a minimum boiling azeotrope with another component or components.

As indicated, tertiary butyl hydroperoxide is useful as a raw material for the manufacture of tertiary butyl alcohol. The tertiary butyl alcohol can be formed by catalytic decomposition of the tertiary butyl hydroperoxide. In the Williams et al. process disclosed in U.S. Pat. No. 3,472,876, an oxygen-containing gas was charged to a reactor containing isobutane and an oxidation catalyst to provide a reaction mixture comprising tertiary butyl alcohol, tertiary butyl hydroperoxide, acetone, and tertiary butyl ether. The reported results in the patent indicate that there was a comparatively low rate of conversion and a comparatively poor selectivity of the reaction to tertiary butyl alcohol.

SUMMARY OF THE INVENTION

In accordance with the present invention, a continuous process is provided wherein isobutane is reacted with oxygen in an oxidation zone to provide an oxidation product comprising a solution of tertiary butyl hydroperoxide and tertiary butyl alcohol in unreacted isobutane. A catalyst may be present to catalyze the reaction of the oxygen with the isobutane if desired.

In accordance with the present invention, the tertiary butyl alcohol solution of tertiary butyl hydroperoxide is continuously fractioned in any suitable manner, e.g. in a distillation zone, to provide a distillation fraction consisting essentially of from about 80 to about 90 wt.% of tertiary butyl hydroperoxide and, correspondingly, from about 20 to about 10 wt.% of tertiary butyl alcohol.

The distillation fraction that is thus-obtained is continuously dissolved in from about 3 to about 10 parts by weight of the monocyclic aromatic solvent per part of tertiary butyl hydroperoxide.

The solvent solution of tertiary butyl hydroperoxide that is charged to the tertiary hydroperoxide decomposition zone will have dissolved or slurried therein from about 0.001 to about 5 wt.%, based on the weight of the tertiary butyl hydroperoxide, of a metal phthalocyanine catalyst.

The catalyst decomposition of the tertiary butyl hydroperoxide is preferably conducted at a temperature within the range of about 10° to about 80° C.

In accordance with a preferred embodiment of the present invention, a continuous method for the preparation of t-butyl alcohol is provided wherein:

1. Isobutane is continuously reacted with molecular oxygen in an oxidation reaction zone under liquid phase oxidation reaction conditions to provide an initial reaction mixture comprising unreacted isobutane and isobutane oxidation reaction products, principally t-butyl hydroperoxide and t-butyl alcohol,
2. Unreacted isobutane is continuously separated from the initial reaction mixture in a first distillation zone to provide a charge stock comprising a solution of t-butyl hydroperoxide in t-butyl alcohol, containing from about 5 to about 50wt.% of t-butyl hydroperoxide,
3. The charge stock is continuously distilled in the distillation zone to provide a second distillate t-butyl alcohol fraction and a third distillation fraction consisting essentially of from about 80 to about 90 wt.% of t-butyl hydroperoxide and, correspondingly, from about 20 to about 10 wt.% of t-butyl alcohol,
4. The third distillate fraction is continuously dissolved in about 3 to about 10 parts by weight, based on the weight of said third distillate fraction of a monocyclic aromatic solvent,
5. The solution to a t-butyl hydroperoxide is continuously charged to a tertiary butyl hydroperoxide decomposition zone and continuously mixed therein with a phthalocyanine decomposition catalyst in an amount constituting from about 0.001 to about 5 wt.%, based on the weight of the t-butyl hydroperoxide in the solution,
6. A hydroperoxide decomposition reaction is continuously conducted in the presence of the phthalocyanine decomposition catalyst in the hydroperoxide decomposition zone in liquid phase with agitation under reaction conditions including a temperature within the range of about 10° to about 80° C. and autogenous pressure or higher to substantially selectively convert the t-butyl hydroperoxide to a decomposition product, principally t-butyl alcohol, and
7. A stream of the hydroperoxide conversion product is continuously withdrawn from said hydroperoxide conversion zone, and tertiary butyl alcohol is continuously recovered from the stream of hydroperoxide conversion product.

The Starting Materials

The starting materials for the present invention include isobutane, oxygen, a suitable monocyclic aromatic hydrocarbon solvent, a phthalocyanine catalyst and, optionally, a promoter for the phthalocyanine catalyst, and a free radical inhibitor.

The isobutane and oxygen are reacted in the manner known to those skilled in the art using oxidation conditions, for example, including a temperature of about 130° to about 160° C., a pressure of about 300 to about 800 psig. and a holding time of about 0.5 to about 5 hours, in order to provide an oxidation product comprising unreacted isobutane, tertiary butyl alcohol, tertiary butyl hydroperoxide and oxygen-containing by-products. Unreacted isobutane is removed from the oxidation product in any suitable manner, conventionally by distillation, to provide a solution comprising tertiary butyl hydroperoxide and oxygen-containing by-products dissolved in tertiary butyl alcohol. The oxidation conditions employed in the oxidation reaction zone are preferably those that will provide a solution of about 5 to about 50 wt.% of tertiary butyl hydroperoxide in tertiary butyl alcohol. More preferably, the oxidation conditions will be adjusted to provide for about a 5 to about a 30 wt.% solution of tertiary butyl hydroperoxide in tertiary butyl alcohol.

In accordance with the present invention, the tertiary butyl alcohol solution of tertiary butyl hydroperoxide is continuously fractioned in any suitable manner, e.g. in a distillation zone, to provide a distillation fraction consisting essentially of from about 80 to about 90 wt.% of tertiary butyl hydroperoxide and, correspondingly, from about 20 to about 10 wt.% of tertiary butyl alcohol. Preferably, the distillation fraction will contain about 90 wt.% of tertiary butyl hydroperoxide.

The distillation fraction that is thus-obtained is continuously dissolved in from about 3 to about 10 parts by weight of the monocyclic aromatic solvent per part of tertiary butyl hydroperoxide and, more preferably, in about 4 to about 7 parts of monocyclic aromatic solvent per part of tertiary butyl hydroperoxide.

The monocyclic aromatic hydrocarbon solvent that is used in accordance with the present invention is suitably benzene, a methyl benzene such as toluene, a xylene, a trimethyl benzene, etc., or a chlorobenzene such as monochlorobenzene, dichlorobenzene, etc.

Metal phthalocyanine catalysts, such as a metal phthalocyanine of the type disclosed in William et al. U.S. Pat. No. 3,816,548, can be used in the method of the present invention.

The metal phthalocyanine catalyst used in this invention is suitably a phthalocyanine of a heavy metal selected from the Group IB, Group VIIB, or Group VIIIB of the Periodic Table.

Phthalocyanine itself is:

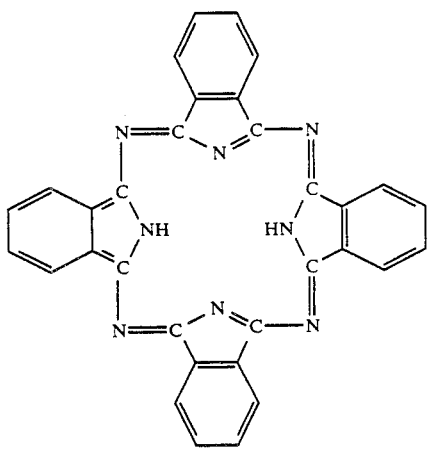

The two hydrogens in the center of the molecule are replaced by metals from these groups. The metals may be in a high oxidation state or a lower oxidation state. For example, Ferric ($Fe^{+++}$) or Ferrous ($Fe^{++}$) may be used. In addition, from 1 to 16 of the peripheral hydrogen atoms on the 4 benzene rings may be replaced with halogen atoms and by numerous organic and inorganic groups. Suitable phthalocyanines include cobalt phthalocyanine, copper phthalocyanine, chromium phthalocyanine, chloroferric phthalocyanine, ferrous phthalocyanine, manganese phthalocyanine, and ruthenium phthalocyanine.

In any event, the solvent solution of tertiary butyl hydroperoxide that is charged to the tertiary hydroperoxide decomposition zone will have dissolved or slurried therein from about 0.001 to about 5 wt.%, based on the weight of the tertiary butyl hydroperoxide, of a metal phthalocyanine catalyst.

The catalyst decomposition of the tertiary butyl hydroperoxide is preferably conducted at a temperature within the range of about 10° to about 80° C. and, more preferably, at a temperature within the range of about 20° to about 40° C. The reaction is preferably conducted at autogenous pressure although superatmospheric pressures up to about 1000 psig. may be used, if desired.

Flow rates of the charge solution to the reaction zone should be adjusted in order to provide an appropriate contact time within the reactor. In a batch process, the holding time may suitably be from about 0.5 to about 10 hours.

DETAILED DESCRIPTION

In accordance with the more preferred embodiment, isobutane is continuously reacted with oxygen in an oxidation zone under oxidation reaction conditions including a temperature of about 135° to about 155° C., a pressure of about 300 to about 800 psig., and a holding time of about 2 to 6 hours to provide an initial oxidation reaction product comprising unreacted isobutane, tertiary butyl hydroperoxide, and some tertiary butyl alcohol. The oxidation reaction product is fractionated in any appropriate manner (e.g., by distillation in a distillation zone) to remove the isobutane therefrom for recycle and to provide a solution of tertiary butyl hydroperoxide and tertiary butyl alcohol which will normally contain from about 5 to about 50 wt.% of tertiary butyl hydroperoxide.

As indicated, the catalytic decomposition of the tertiary butyl hydroperoxide in the catalytic hydroperoxide decomposition reaction zone may suitably be conducted at a temperature within the range of about 10° to 80° C. (and more preferably from about 20° to about 40° C.) at autogenous pressure or if desired at a superatmospheric pressure up to 1000 psig. for a contact time within the range of about 0.5 to about 10 hours.

Unreacted isobutane is removed from the oxidation product in any suitable manner, conventionally by distillation, to provide a solution comprising tertiary butyl hydroperoxide and oxygen-containing by-products dissolved in tertiary butyl alcohol.

In accordance with the present invention, the debutanized solution of tertiary butyl hydroperoxide in tertiary butyl alcohol is additionally continuously fractionated in the distillation zone to provide a distillate tertiary butyl alcohol fraction and a distillation fraction consisting essentially of from about 80 to about 90 wt.% of tertiary butyl hydroperoxide and, correspondingly, about 20 to about 10 wt.% of tertiary butyl alcohol. More preferably, the distillation fraction will consist essentially of about 90 wt.% of tertiary butyl hydroperoxide and about 10 wt.% of tertiary butyl alcohol.

The distillation fraction is then continuously dissolved in from about 3 to about 10 parts by weight of a monocyclic aromatic solvent and more preferably, from about 4 to about 8 parts by weight of the monocyclic aromatic solvent.

It is frequently advantageous to add a promoter for the phthalocyanine catalyst to the reaction mixture in the tertiary butyl hydroperoxide decomposition zone. When this is done, from about 1 to about 5 parts by weight of the promoter should be used for each part by weight of the phthalocyanine catalyst.

Any suitable base having a pH of greater than about 7.5 when 0.10 mole is dissolved in 1 liter of water may be used as a promoter. For example, the promoter may be an alkali metal carbonate, bicarbonate, acetate, hydrogen phosphate, formate, benzonate, etc.

Representative examples of suitable promoters include materials such as sodium acetate, sodium carbonate, sodium bicarbonate, etc., sodium acetate, sodium formate, etc., lithium carbonate or bicarbonate, etc., potassium benzoate, etc.

Heterocyclic amines such as pyridine, quinoline, isoquinoline, imidazole, 1-alkyl imidazoles, 2-alkyl imidazoles (wherein the alkyl group contains 1 to 4 carbon atoms) such as 1-methyl imidazole, 2-methyl imidazole, etc., may also be used.

As as another example, metal borates may be used as promoters, including alkali metal borates, alkaline earth metal borates, and borates of metals of Group IA, Group IIA or Group IIB. Examples of appropriate metal borates include compounds such as sodium borate, lithium borate, magnesium borate, zinc borate, calcium borate, barium borate, sodium metaborate, lithium metaborate, ammonium borate, etc.

SPECIFIC EXAMPLES

The invention will be further illustrated by the following specific examples which are given by way of illustration and not as limitations on the scope of this invention.

Solvent and catalyst were charged to a 250-ml 3-necked round bottom flask equipped with a stirrer, thermometer, water cooled condenser and water bath. A tube led from the top of the condenser to a water filled gas buret. TBHP was added all at once to the stirred mixture, the flask sealed and the volume of gas (oxygen) given off at specified time intervals noted. A semilog plot of $V\infty\text{-}V$ versus time gave a pseudo first order rate constant. The data given in the following table were determined by linear regression analysis of the data.

TABLE I

| | | | | | | | Additive | | | Inhib.[c] | | | | | |
|---|---|---|---|---|---|---|---|---|---|---|---|---|---|---|---|
| N.B. Number | TBHP 90%, g | Solvent[a] ID | (g) | Catalyst[b] ID | (g) | | ID | (g) | Temp. (°C.) | Time (min.) | $10^3 k^d$ min-1 | $R^e$ | $t\frac{1}{2}^f$ (min) | No.[g] Pts. | Fe[h] ppm |
| 6400-86 | 6.6 | TBA | 17.4 | Fe(III)PCYCl | 0.20 | | None | 0.0 | 25 | 4 | 24.6 | 0.962 | 28.2 | 17 | 22 |
| 6400-77 | 6.6 | TBA | 17.4 | Fe(III)PCYCl | 0.20 | | Imidazole | 0.05 | 25 | 10 | 44.7 | 0.906 | 15.5 | 10 | 11 |
| 6404-7 | 6.0 | ACN | 18.0 | Fe(III)PCYCl | 0.20 | | None | 0.0 | 25 | 0.5 | 254 | 0.995 | 2.7 | 13 | 14 |
| 6404-9 | 5.0 | ACN/TBA | 9.0/9.0 | Fe(III)PCYCl | 0.20 | | None | 0.0 | 24 | 2 | 92.1 | 0.993 | 7.5 | 18 | 24 |
| 6404-10 | 5.0 | ACN/TBA | 4.0/14.0 | Fe(III)PCYCl | 0.20 | | None | 0.0 | 25 | 2 | 49.9 | 0.995 | 13.9 | 21 | 26 |
| 6404-15 | 5.0 | CCl4 | 18.0 | Fe(III)PCYCl | 0.20 | | None | 0.0 | 24 | <0.5 | 54.4 | 0.998 | 12.7 | 27 | 10 |
| 6404-16 | 5.0 | MCB | 18.0 | Fe(III)PCYCl | 0.20 | | None | 0.0 | 25–45 | ~0 | ~693 | — | ~1 | — | 24 |
| 6404-17 | 5.0 | Toluene | 18.0 | Fe(III)PCYCl | 0.20 | | None | 0.0 | 23–42 | ~0 | ~462 | — | ~1.5 | — | 12 |
| 6404-33 | 5.0 | Toluene | 36.0 | Fe(III)TPPCl | 0.40 | | None | 0.0 | 24–50 | ~0 | — | — | <1 | — | — |
| 6404-36 | 5.0 | Toluene | 36.0 | Fe(III)TPPCl | 0.40 | | None | 0.0 | 23–34 | ~0 | — | — | <1 | — | — |

[a]TBA = tert-butyl alcohol; ACN = acetonitrile; CCl4 = carbon tetrachloride; MCB = monochlorobenzene
[b]Fe(III)PCYCl = chloroferric phthalocyanine; Fe(III)TPPCl = Iron(III)tetraphenylporphine chloride
[c]Inhibition time = defined as time for 1% reaction to occur
[d]Pseudo first order rate constant
[e]R = correlation coefficient
[f]t ½ = half-life in minutes
[g]No. of points in rate determination
[h]% iron determined on filtered reaction mixture after reacting for 10 half lives In Table I experiment No. 6400-86 where TBA is the solvent the decomposition rate is moderately fast showing a decomposition half life of 28.2 minutes. The decomposition is faster (half life 15.5 minutes) when imidazole is used as an additive to the phthalocyanine catalyst (6400-77). Inhibition time increased from 4 to 10 minutes. The reaction rate when acetonitrile is used as solvent is faster showing a half life of 2.7 minutes (6404-7). When a mixture of acetonitrile and TBA is used the rate falls between that of pure acetonitrile and pure TBA (6404-9, 6404-10). Carbon tetrachloride as solvent (6404-15) shows a faster rate of decomposition than TBA, but still not as fast as the aromatic solvents. Monochlorobenzene and toluene are the best solvents for acceleration of the rate of decomposition--half lives on the order of 1-2 minutes and indeed so fast that only an approximate rate of decomposition can be measured. In metal ion catalyzed decompositions of hydroperoxides, one does not expect a large effect on the rate of decomposition when solvents are changed.

Having thus described our invention, what is claimed is:

1. In a continuous method for preparing t-butyl alcohol wherein isobutane is continuously reacted with molecular oxygen in an oxidation reaction zone under liquid phase oxidation reaction conditions to provide an initial reaction mixture comprising unreacted isobutane and isobutane oxidation reaction products, principally t-butyl hydroperoxide and t-butyl alcohol, and wherein unreacted isobutane is continuously separated from said initial reaction mixture in a distillation zone to provide a charge stock comprising a solution of said t-butyl hydroperoxide in said t-butyl alcohol, containing from about 5 to about 50 wt.% of t-butyl hydroperoxide, the improvement which comprises:
   (a) continuously distilling said charge stock in distillation zone to provide a second distillate t-butyl alcohol fraction and a third distillation fraction consisting essentially of from about 80 to about 90 wt.% of t-butyl hydroperoxide and, correspondingly, from about 20 to about 10 wt.% of t-butyl alcohol,
   (b) continuously dissolving said third distillate fraction in about 3 to about 10 parts by weight, based on the weight of said third distillate fraction, of a monocyclic aromatic solvent,
   (c) continuously charging said solution to a t-butyl hydroperoxide decomposition zone,
   (d) continuously adding a phthalocyanine decomposition catalyst to said solution in an amount constituting from about 0.001 to about 5 wt.%, based on the weight of the t-butyl hydroperoxide in said solution,
   (e) continuously conducting a hydroperoxide decomposition reaction in the presence of said phthalocyanine decomposition catalyst in said hydroperoxide decomposition zone in liquid phase with agitation under reaction conditions including a temperature within the range of about 10° to about 80° C. and autoqenous pressure to convert said t-butyl hydroperoxide to decomposition products, principally t-butyl alcohol and to thereby provide a hydroperoxide conversion product,
   (f) continuously removing a stream of said hydroperoxide conversion product from said hydroperoxide conversion zone, and
   (g) continuously recovering t-butyl alcohol from said stream of said hydroperoxide conversion product.

2. A method as in claim 1 wherein a basic promoter for the phthalocyanine catalyst is also added to the solution in the t-butyl hydroperoxide decomposition reaction zone.

3. A method as in claim 2 wherein the basic promoter is an imidazole.

4. A method as in claim 2 wherein the basic promoter is an alkali metal carbonate, bicarbonate, acetate or hydrogen phosphate.

5. A method as in claim 2 wherein the basic promoter is a borate.

6. A method as in claim 2 wherein the basic promoter is an amine.

7. In a continuous method for preparing t-butyl alcohol wherein isobutane is continuously reacted with molecular oxygen in an oxidation reaction zone under liquid phase oxidation reaction conditions to provide an initial reaction mixture comprising unreacted isobutane and isobutane oxidation reaction products, principally t-butyl hydroperoxide and t-butyl alcohol, and wherein unreacted isobutane is continuously separated from said initial reaction mixture in a distillation zone to provide a charge stock comprising a solution of said t-butyl hydroperoxide in said t-butyl alcohol, containing from about 5 to about 50 wt.% of t-butyl hydroperoxide, the improvement which comprises:
   (a) continuously distilling said charge stock in said distillation zone to provide a second distillate t-butyl alcohol fraction and a third distillation fraction consisting essentially of about 90 wt.% of t-butyl hydroperoxide and, correspondingly, about 10 wt.% of t-butyl alcohol,
   (b) continuously dissolving said third distillate fraction in about 4 to about 8 parts by weight, based on the weight of said third distillate fraction of a solvent selected from the group consisting of benzene, methyl benzenes and chlorobenzenes,
   (c) continuously charging said solution to a t-butyl hydroperoxide decomposition zone,
   (d) continuously adding a base-promoted phthalocyanine decomposition catalyst to said solution in an amount constituting from about 0.001 to about 5 wt.%, based on the weight of the t-butyl hydroperoxide in said solution,
   (e) continuously conducting a hydroperoxide decomposition reaction in the presence of said phthalocyanine decomposition catalyst in said hydroperoxide decomposition zone in liquid phase with agitation under reaction conditions including a temperature within the range of about 20° to about 40° C. and autogenous pressure to convert said t-butyl hydroperoxide to decomposition products, principally t-butyl alcohol and to thereby provide a hydroperoxide conversion product,
   (f) continuously removing a stream of said hydroperoxide conversion product from said hydroperoxide conversion zone, and
   (g) continuously recovering t-butyl alcohol from said stream of said hydroperoxide conversion product.

8. A method as in claim 7 wherein a solvent is toluene.

9. A method as in claim 7 wherein a solvent is monochlorobenzene.

* * * * *